(12) United States Patent
Lewitus et al.

(10) Patent No.: US 10,967,346 B2
(45) Date of Patent: Apr. 6, 2021

(54) MICROSPHERES AND METHOD FOR PRODUCING THEM

(71) Applicant: SHENKAR ENGINEERING DESIGN ART, Ramat Gan (IL)

(72) Inventors: Dan Lewitus, Herzliya (IL); Tal Shpigel Shtauber, Tel Aviv (IL)

(73) Assignee: Shenkar Engineering Design Art, Ramat Gan (IL)

( * ) Notice: Subject to any disclaimer, the term of this patent is extended or adjusted under 35 U.S.C. 154(b) by 0 days.

(21) Appl. No.: 16/331,764

(22) PCT Filed: Sep. 11, 2017

(86) PCT No.: PCT/IL2017/051022
§ 371 (c)(1),
(2) Date: Mar. 8, 2019

(87) PCT Pub. No.: WO2018/047185
PCT Pub. Date: Mar. 15, 2018

(65) Prior Publication Data
US 2019/0270060 A1    Sep. 5, 2019

Related U.S. Application Data

(60) Provisional application No. 62/393,033, filed on Sep. 11, 2016, provisional application No. 62/556,459, filed on Sep. 10, 2017.

(51) Int. Cl.
*B01J 2/06* (2006.01)
*A61K 9/50* (2006.01)
*B01J 2/02* (2006.01)

(52) U.S. Cl.
CPC .............. *B01J 2/06* (2013.01); *A61K 9/5015* (2013.01); *A61K 9/5089* (2013.01); *B01J 2/02* (2013.01)

(58) Field of Classification Search
CPC .. B01J 2/02; B01J 2/06; A61K 9/5015; A61K 35/06; A61K 9/5063; A61K 9/5089
See application file for complete search history.

(56) References Cited

U.S. PATENT DOCUMENTS

| 7,993,677 | B2 * | 8/2011 | Ding | A61K 8/0283 |
| | | | | 424/489 |
| 8,445,023 | B2 | 5/2013 | Guimberteau et al. | |
| 8,722,091 | B2 | 5/2014 | Brynjelsen et al. | |
| 8,765,182 | B2 | 7/2014 | Day et al. | |
| 9,102,081 | B2 | 8/2015 | Hielscher et al. | |
| 2013/0147074 | A1 * | 6/2013 | Hielscher | B29B 9/10 |
| | | | | 264/13 |
| 2014/0205804 | A1 | 7/2014 | Jones et al. | |
| 2015/0361227 | A1 | 12/2015 | Schmidt et al. | |
| 2015/0375429 | A1 * | 12/2015 | Butt | B01J 2/04 |
| | | | | 427/457 |

OTHER PUBLICATIONS

Milionis et al., "Recent advances in oil-repellent surfaces", International Materials Reviews, 2016, 1743-2804.
Rial-Hermida et al., "Bioinspired superamphiphobic surfaces as a tool for polymer-and solvent-independent preparation of drug-loaded spherical particles", 2014, Acta Biomaterialia, vol. 10, pp. 4314-4322.

* cited by examiner

*Primary Examiner* — Blessing M Fubara
(74) *Attorney, Agent, or Firm* — Vorys, Sater, Seymour and Pease LLP; Anthony Venturino

(57) ABSTRACT

Provided is an organic solvent-free method for producing a plurality of microsphere having an average diameter of less than 500 μm in diameter and having average contact angle θc greater than 140°, consisting essentially of a biocompatible hot-melt carrier vehicle and a payload substance to be delivered, including melting and mixing a polymer carrier vehicle which is solid at room temperature and at least one payload substance, and dispensing microportions of the molten mixture through a droplet-forming space onto a cooled solid superoleophobic surface.

16 Claims, 17 Drawing Sheets

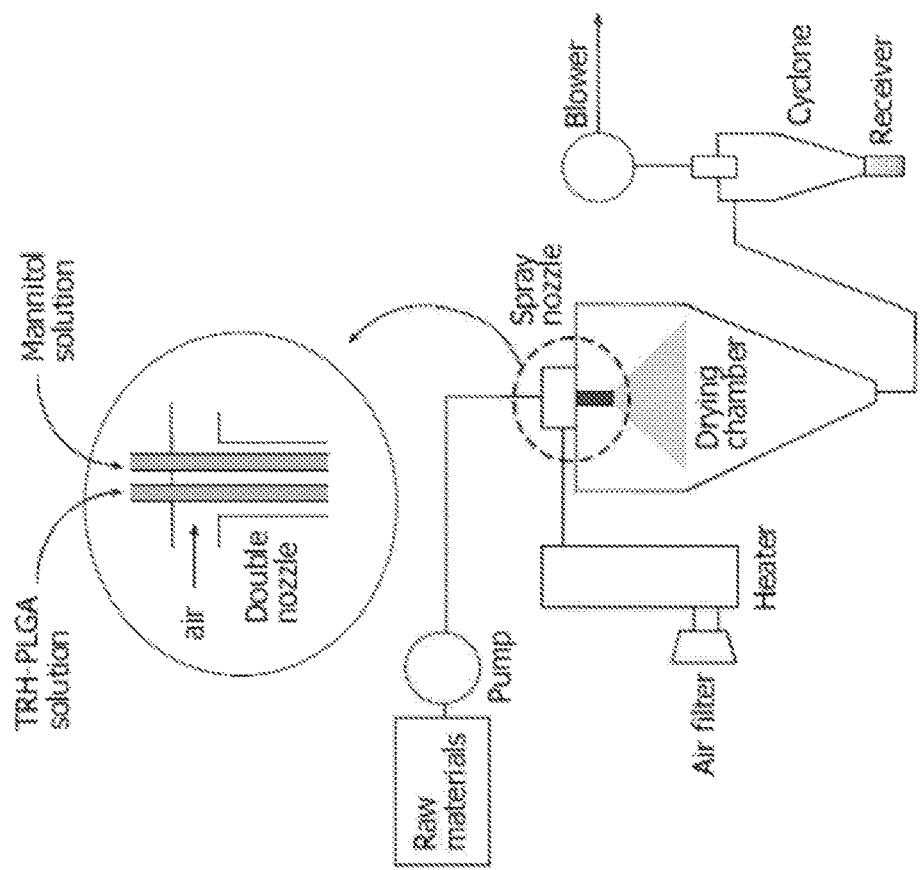
FIG. 1C
PRIOR ART
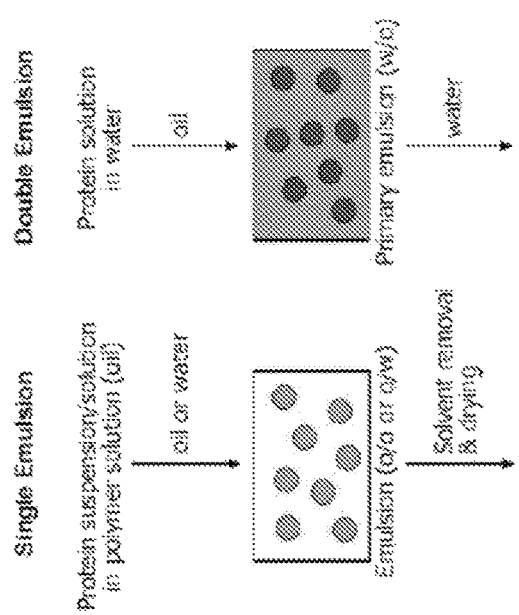
FIG. 1A
FIG. 1B
PRIOR ART

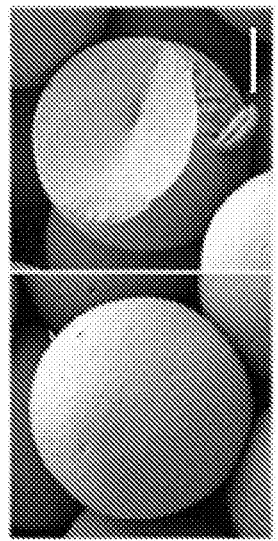
FIG. 1D Microspheres
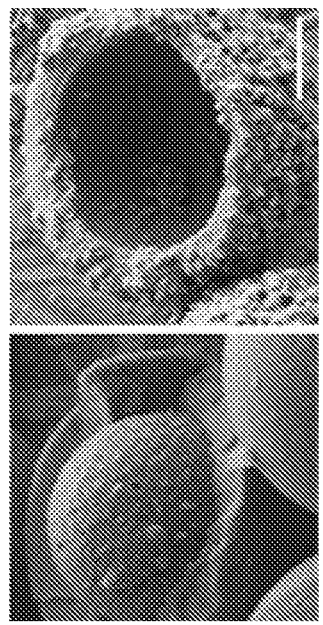
FIG. 1F Microcapsules
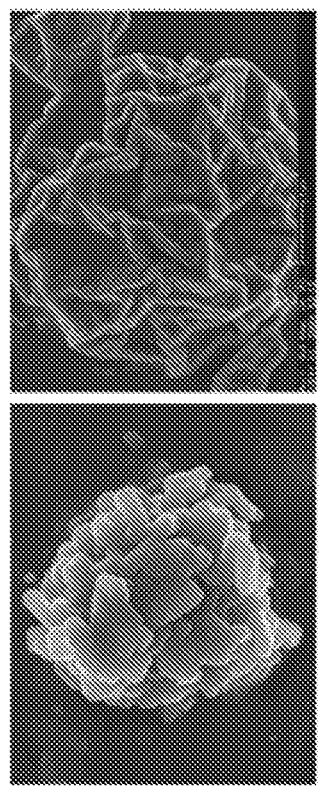
FIG. 1E Microparticles

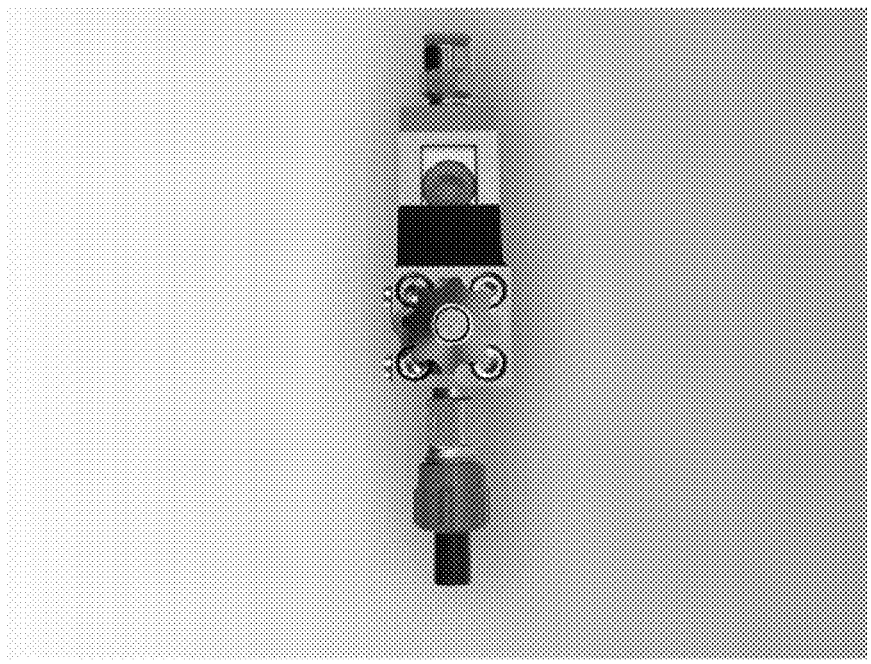
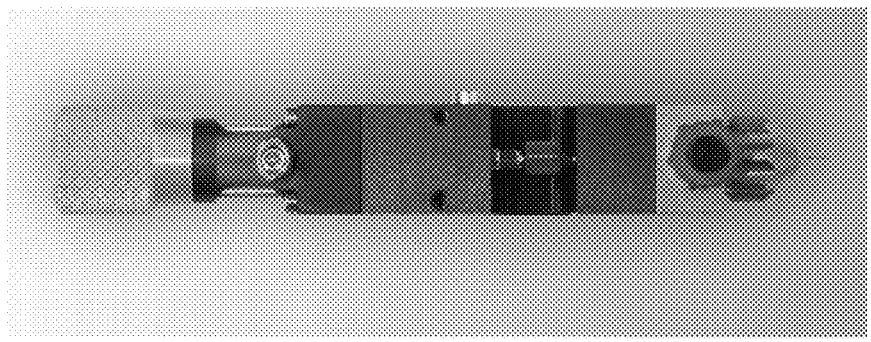
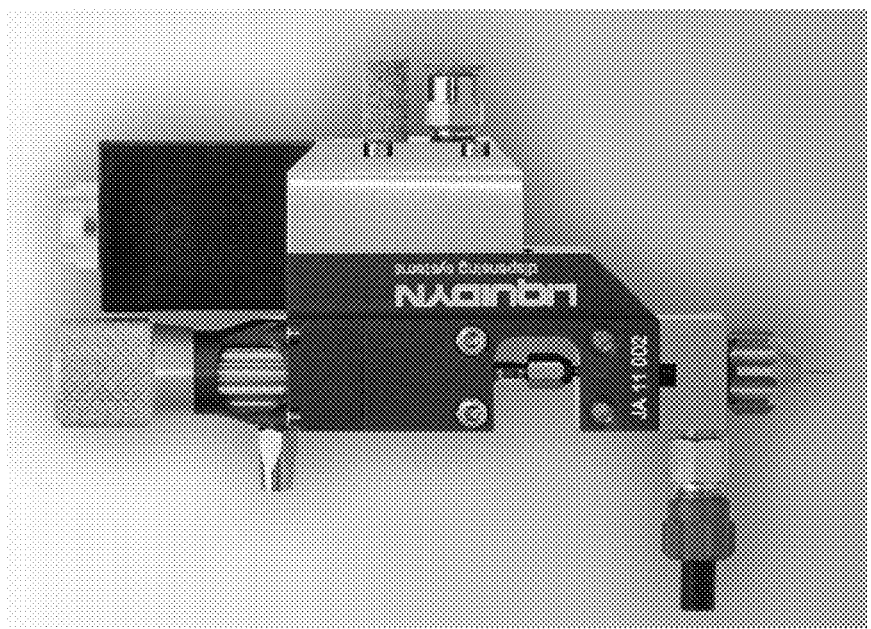

| | Solvent evaporation (literature) | Printed microspheres on superoleophobic surfaces |
|---|---|---|
| | 30%IBU-PCL | 30%IBU-PCL (-20) |
| EE (%) | 67.3 | 95.3 ± 2.7 |

FIG. 5

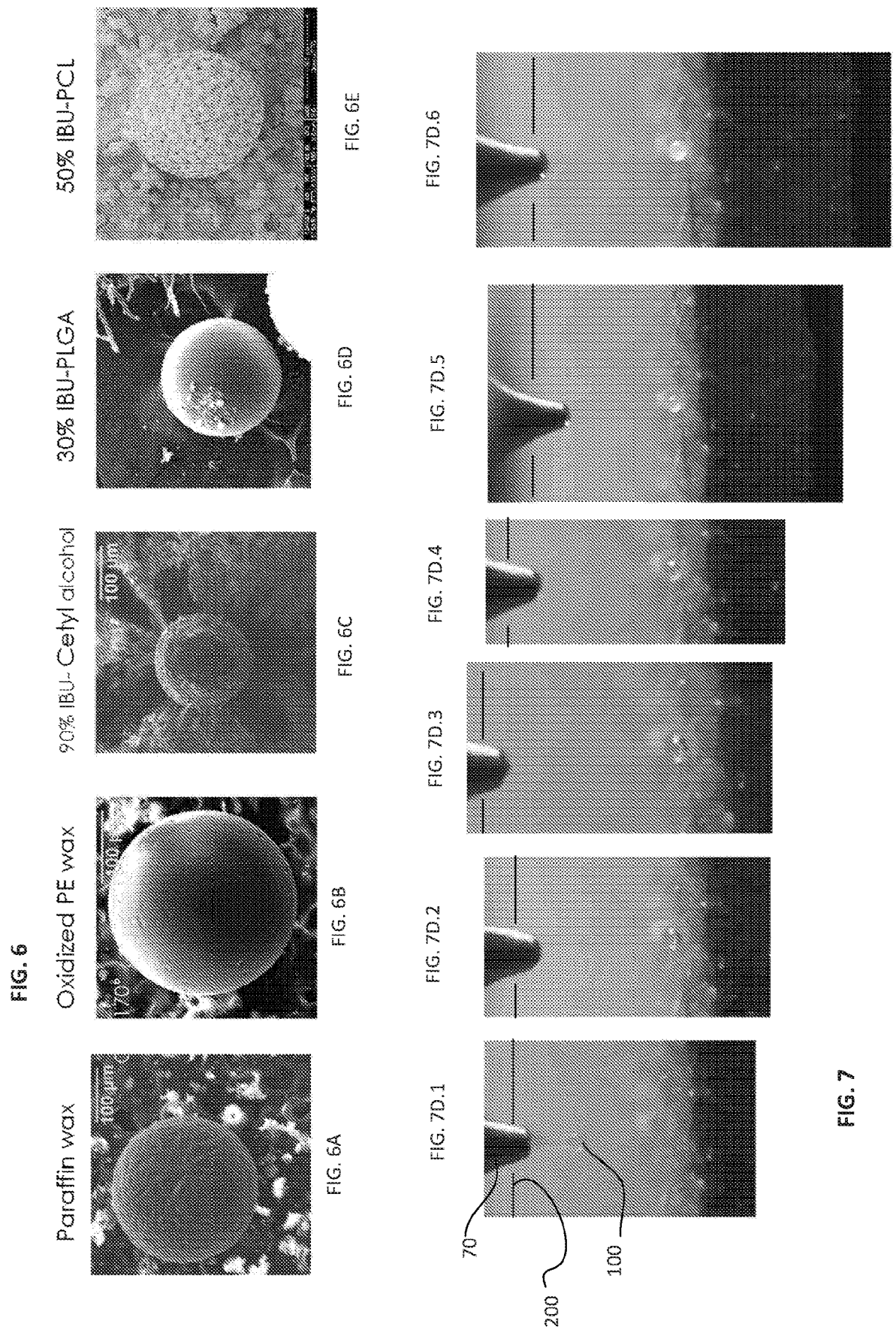

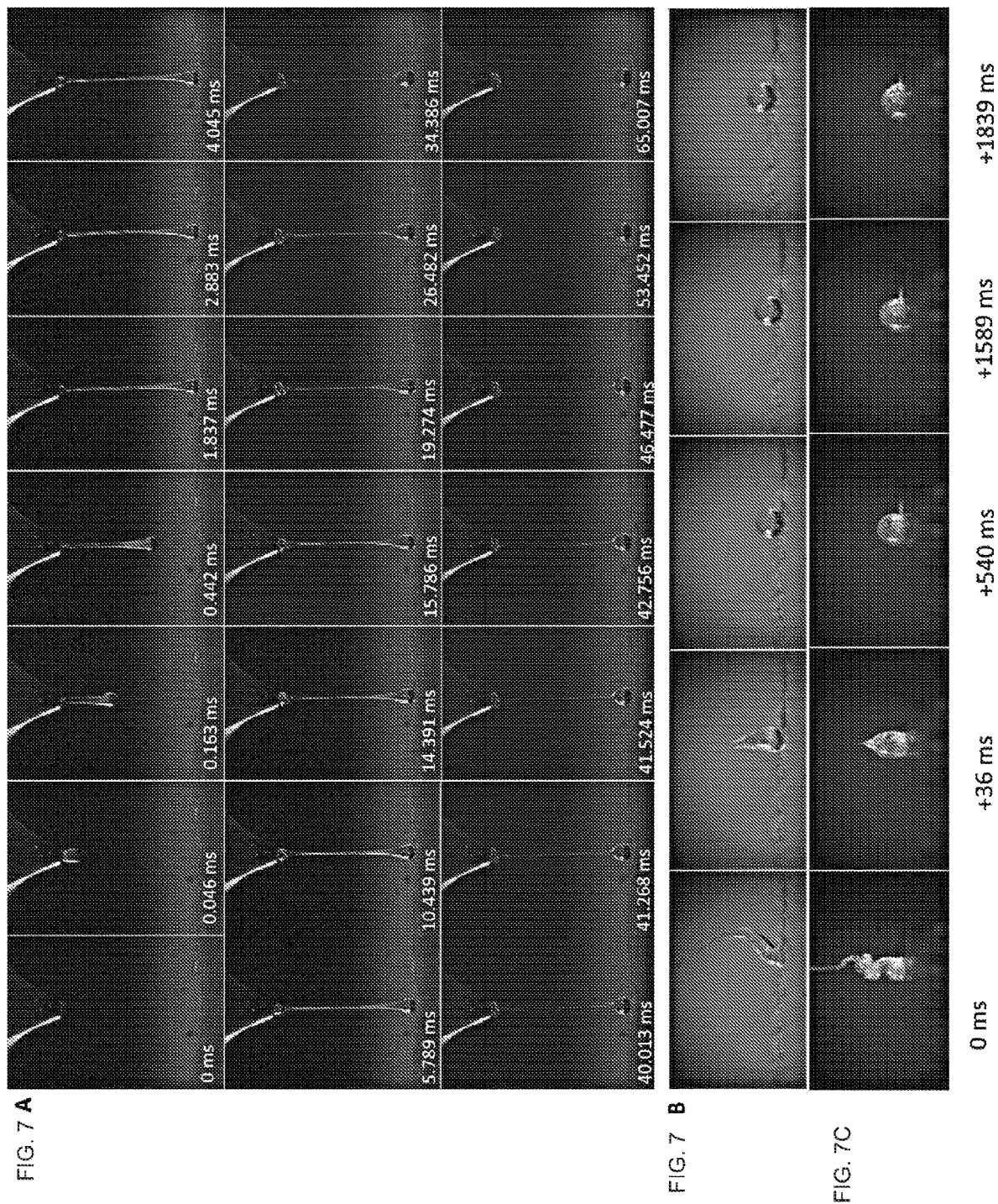

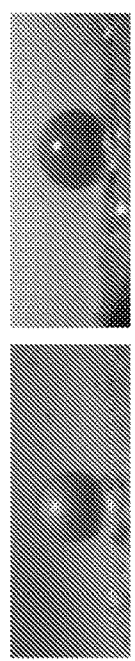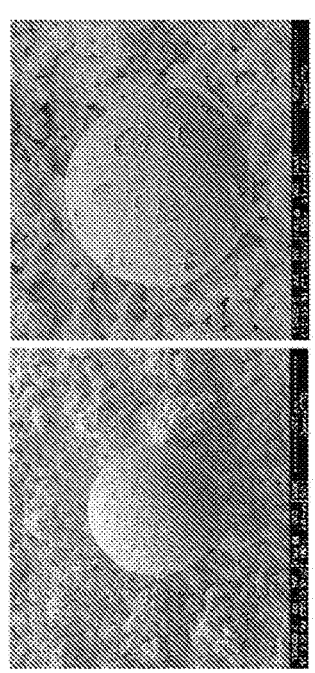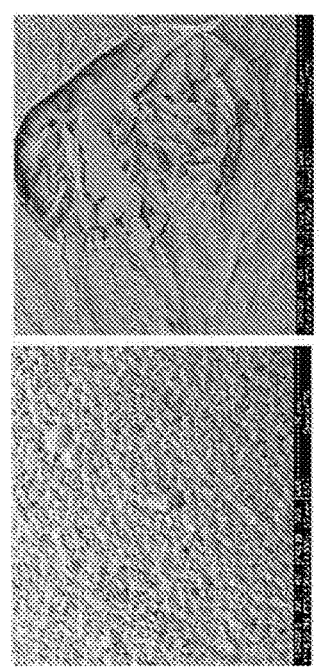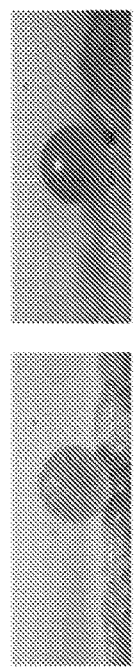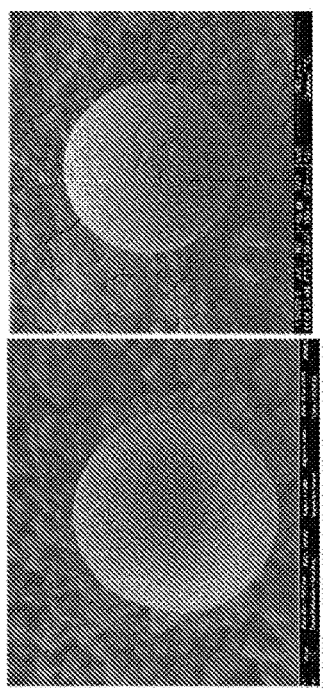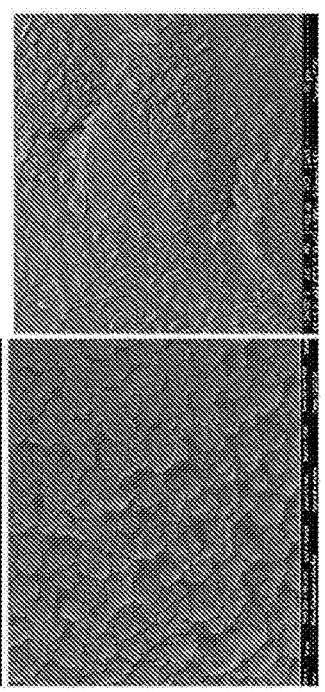
FIG. 8D  FIG. 8E  FIG. 8F  FIG. 8G

MICROSPHERES AND METHOD FOR PRODUCING THEM

FIELD OF THE DISCLOSED TECHNIQUE

The disclosed technique relates to microspheres and techniques for producing them, in general, and to methods and for producing drug-carrying and drug-dispensing microspheres, in particular.

BACKGROUND OF THE DISCLOSED TECHNIQUE

Known methods for reliably and economically producing microspheres, in scalable quantities, are not suitable for many applications.

In particular, known methods for making microspheres which are intended for use as drug-carrying and -dispersal agents have not answered the needs of a variety of desirable delivery routes.

In the production of pharmaceutical-grade microspheres issues such as biocompatibility, antigenicity, toxicity, pharmacokinetics, medication release profile, reproducibility, contaminant avoidance, and numerous other factors have to be taken into consideration.

Unfortunately, many of these needs are not fulfilled for a variety of situations in which microsphere drug delivery would be good for patients, health providers, regulators, pharmaceutical companies and payors.

Additional examples of areas where microspheres are found include personal care and cosmetics, household care in the form of washing powders, in paints and coatings, in the food industry, in agriculture for fertilizers, and in electronic papers.

Methods for making microspheres such as solvent evaporation, spray draing in fluidized beds and using microfluidic channels all have drawbacks. These include but are not limited to: solvent and surfactant residue and removal (patient safety and ecological/environmental considerations), capacity-limiting drug loss (efficiency), low yields, poor scalability, and challenging reproducibility often requiring one or more separation steps for winnowing out the substandard particles.

Looking particularly at microspheres in the field of drug delivery, as an example only, microspheres are particularly useful for respirable drugs as well as injectable. However, they could also be used in specialty areas such as for ophthalmological or other ENT indications, in transdermal, oral and other routes of administration.

The spherical form has many advantages including flowability, high surface area to volume ratio and compact packing efficiency.

U.S. Pat. No. 9,102,081B2 to Hielscher discloses solidification of a molten material. The disclosed method for making droplets are via atomization.

Patent Publication US2015375429A1 to Butt does not describe deposition of a melt and cooling it.

US20150361227A1 and WO2014124751A1 to Schmidt disclose spray drying materials and polymerizing monomers into capsules.

US20150375429A1 discloses how to make surfaces.

U.S. Pat. No. 8,765,182 to Day discloses a form of liquid-liquid phase separation process that uses solvents.

U.S. Pat. No. 8,722,091 to Baxter discloses sonicated lyophilization that is submicron. It is a solvent based process that is multi-staged and complicated.

U.S. Pat. No. 8,445,023 to Flamel describes a specific coating process of microspheres (e.g. fluidized bed).

SUMMARY OF THE PRESENT DISCLOSED TECHNIQUE

It is one object of the disclosed technique to provide a novel method and system for manufacturing microspheres in specific size ranges.

It is another object of the disclosed technique to provide a novel method and system for manufacturing microspheres which produces microspheres using a carrier vehicle which is easy to handle.

It is still another object of the disclosed technique to provide a novel method and system for manufacturing microspheres using a carrier vehicle which contains desirable amounts of a payload substance, such as an active pharmaceutical ingredient.

It is still another object of the disclosed technique to provide a novel method and system for manufacturing microspheres which uses no solvents other than the molten carrier vehicle.

It is yet another object of the disclosed technique to provide a novel method and system for manufacturing microspheres which is environmentally sound.

In accordance with the disclosed technique, there is thus provided one exemplary embodiment of a method for producing microspheres less than 500 μm in radius that have substantially (at least 75%) spherical outer surfaces comprising a biocompatible hotmelt carrier vehicle (or excipient) and a payload substance to be delivered, where the payload substance has a melting point suitably similar to that of the carrier vehicle, comprises the following procedure;

a. melting carrier vehicle material in one reservoir and, optionally, melting or simply holding payload substance in a thermally separated reservoir;

b. mixing, dissolving or dispersing the payload substance into the molten carrier vehicle in a mixing reservoir; and c. forming microdroplets by pushing, by application of pulsatile pressure (or by applying constant pressure and cycling between opening and closing an extrusion valve, or some combination of both), the molten carrier vehicle/payload substance solution or dispersion through at least one orifice, into a microdroplet-forming space and deposited onto a microsphere cooling surface.

An alternative exemplary embodiment of a method for producing microspheres, having an average radius of less than 1000 μm, preferably less than 500 μm, and having substantially (at least 75%) spherical outer surfaces, consisting of a biocompatible hot-melt carrier vehicle and a payload substance to be delivered, comprises the following procedure;

a. mixing solid carrier vehicle and solid payload substance, b. heating the mixture until at least the carrier vehicle is liquefied and the mixture is turned into a dispersion or solution, c. forming microdroplets by pushing, by application of pulsatile pressure (or by applying constant pressure and cycling between opening and closing an extrusion valve, or some combination of both), the molten carrier vehicle/payload substance solution or dispersion through at least one orifice, into a microdroplet-forming space and onto a collecting surface.

or c. pushing portions of the molten mixture through at least one orifice (apportionment occurring by pulsatile application of pressure to the molten mixture or by cycling between opening and closing an extrusion valve at the orifice while applying constant, but low pressure to the molten mixture), and d. permitting droplets to drip from the at least one orifice into at least one droplet-forming space, possibly comprising a gas atmosphere, and onto a collecting surface which may comprise a solid surface set at a sufficiently great distance (from about 1 mm to about 4 mm) and time (possibly reached via a steeply angled parabolic-like curving surface or trough) from the at least one orifice to permit substantial droplet separation, and sphere formation and solidification to occur. In another exemplary embodiment gentle non-deforming collection of the still-cooling microdroplets may be achieved by collecting the droplets onto a superoleophobic soft and loose fibrous weave such as an aerogel having a porosity substantially larger and a depth at least one or two times the diameter of the desired microspheres through which the microdroplets can gently drop as they finish cooling.

BRIEF DESCRIPTION OF THE DRAWINGS

The disclosed technique will be understood and appreciated more fully from the following detailed description taken in conjunction with the drawings in which:

FIGS. 1A-1C show prior art methods for producing microspheres and FIGS. 1D-1F illustrate what are thought of as generally representative of microspheres, microparticles and microcapsules, respectively;

FIGS. 2A-2E are illustrations taken from the manufacturer's literature for apparatus which has been adapted and configured to be used to practice the techniques of the exemplary embodiments;

FIG. 5 shows a comparison of the average process efficiency of 67.3% for making 30% IBU-PCL microspheres as reported in the prior art versus 95.3%±2.7% for producing 30% IBU-PCL microspheres according to the inventive techniques at −20° C.;

FIGS. 6A-6D show SEM images of microspheres of various compositions, at different magnifications, all produced according to the inventive techniques;

FIG. 7A shows a sequence of frames from high speed video showing the formation of a single microsphere using the disclosed techniques in a time lapse of about 65 ms;

FIG. 7B shows a sequence of frames showing a time lapse of about 500 ms between the moment just after the melt contacts the superoleophobic surface and the time it gathers into a sphere having contact angle $\theta_c$ greater than about 1400;

FIG. 7C shows a sequence of frames showing that after 1800 ms only a hemisphere is formed by the same melt on untreated aluminum surface;

FIG. 7D is a time lapse sequence of 6 photos spanning about 6 seconds from a droplet 10 of melt dropping in D1, landing and gathering into a sphere in D3, to final cooled state in D6;

FIGS. 8A-G show PCL microspheres and IBU-PCL microspheres having measured size and sphericity, produced using the disclosed techniques with varying parameters of temperature and content;

DETAILED DESCRIPTION OF THE EMBODIMENTS

Figure 2D:
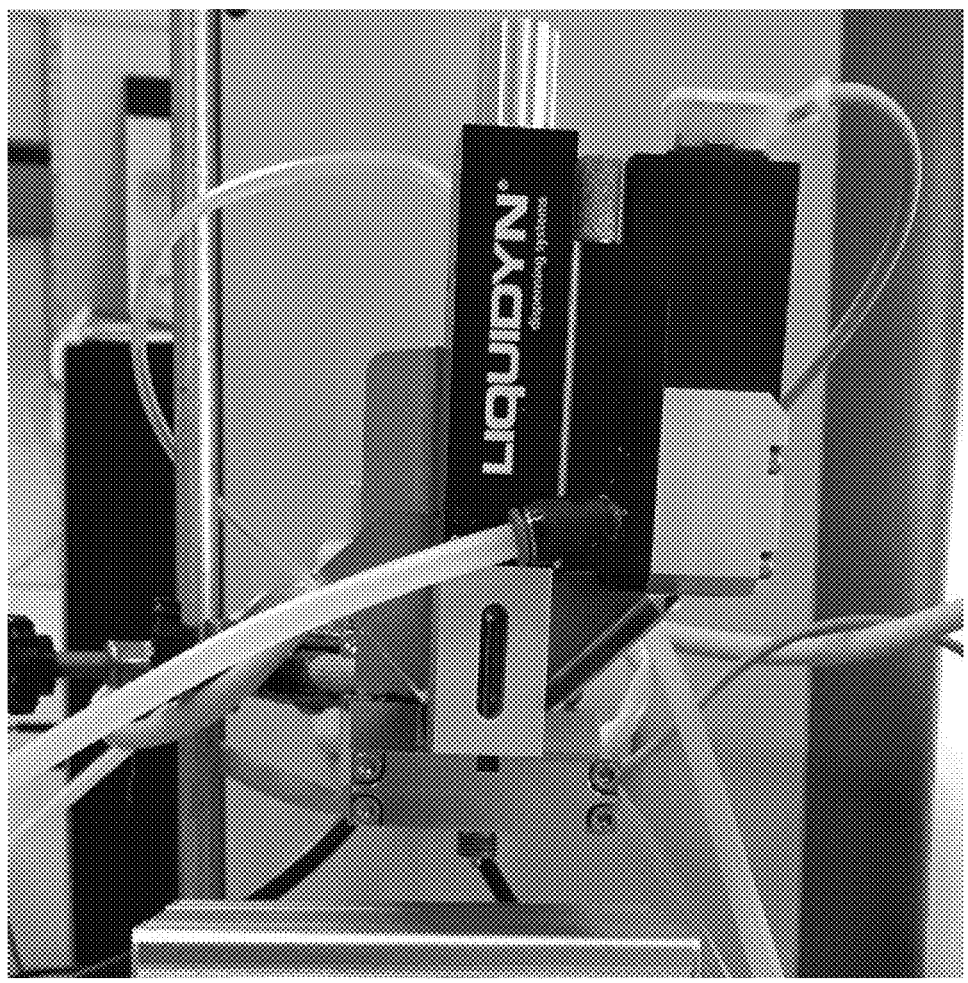
Figure 2E:

The Examples and Techniques have been developed using the following equipment and materials:

Liquidyn GmbH's V100 Controller unit (see FIG. 3) for controlling Liquidyn's high precision micro dispensing valves P-Dot and P-Jet. (See FIGS. 2A-C)

Polycaprolactone ("PCL");
Paraffin wax with melting point 53-57° C.;
Paraffin wax with mp. 58-62° C.;
Paraffin wax mp.>62° C.;
cetyl alcohol ("CA") mp. 49° C.;

Low density Oxidized Polyethylene (LDOxPE) homopolymer in prill form for use in solvent borne coatings as a rheological aid. It also finds use as a metal release agent in PVC. It is a pigment dispersing agent for color masterbatch. It can also be atmospherically emulsified for use in aqueous applications, such as textiles, lubricants, coatings and inks, to lower the COF and provide surface properties such as mar & abrasion resistance and increased slip. Honeywell A-C® 629A Oxidized PE homopolymer sold as a Slip Agent/Lubricant/Mold Release/Processing Aid Additive.

AClyn® 201 Calcium ionomer of an EAA copolymer. a low molecular weight ionomer marketed by Honeywell. AClyn® A-C 201 is a synthetic wax which is designed to influence many properties, including mar resistance, abrasion resistance, slip, matting, adhesion and release feel. It is flexible enough for use in water or solvent-based thin film applications.

VISCOWAX® 122 PE-Wax
Licowax PE 520 powder PE wax
Luwax® A (BASF)
DuPont™ Elvaloy® AC 1820 (ethylene methyl acrylate copolymer)
Polycaprolactone ("PCL")
Poly (lactic-co-glycolic acid) copolymer ("PLGA")

Definitions

Microspheres—means substantially spherical, mostly solid, particles or balls. Can include spheres with radii as large as 500 μm to as small as tenths, and possibly even hundredths of a micron. For purposes of this application, the terms microbeads, is synonymous.

Microdroplets—means substantially or completely molten portions of just dispensed melt (whether or not API is molten, dissolved or dispersed), having just separated from the dispensing nozzle and which is earliest stage in the process of forming and hardening into a microsphere. They will have a range in size and shape similar to that of the relevant microspheres, though changing from stretched teardrop to spherical.

Satellites—small particles, 10% or less of the targeted microsphere size, which may form on or possibly separated and cooled apart from the main volume of a microdroplet. They may result from impact, impurities in the material used, pressure-induced spatter, material buildup around a nozzle orifice, etc.

Solidification vs. stabilization—the microspheres of the present technique are substantially solid spheres, with few if any empty air spaces. However, it is recognized that there can be a significant difference between the time for a sphere to fully cool to ambient temperature and the outer shape of a molten sphere to assume a fairly stable spherical shape. In general, the techniques herein are most concerned with achieving a stable sphere within as few as fractions of a second to mere seconds after the microdroplet is ejected from the nozzle. However, a substantial portion of the techniques and technology are concerned with safeguarding sphericity as solidification fully occurs. Thus a distinction is made between a sphere which is stable in the sense that its outer shape has been fairly well determined but it's outer morphology is still potentially vulnerable to change by impacts and temperature shocks versus a microsphere which is substantially or fully solidified and hence has outer morphology that is far less vulnerable to shape-changing factors.

Carrier vehicle—also referred to herein as excipient or matrix material, this is a biocompatible hot-melt delivery material, i.e. it can be heated to change phase from solid to flowing, then dispensed and cooled back to solid. A non-exhaustive and non-limiting list of examples of suitable materials for carrier vehicle includes:

polyolefins $C_{20}$ and higher (polyolefin waxes and polyolefins)—including preferably highly saturated and only slightly unsaturated polyolefins, modified polyolefin waxes (oxidized, ester, amine, amide etc.), polyamides, polyvinyls, biodegradable polyesters (including polylactic acid, polyglycolic acid, polycaprolactone and their copolymers), polyurethanes, polycarbonates, polyacrylates, fatty acids, fatty alcohols, aliphatic alkyl amines, lipids, including fatty alcohols, fatty acids, fatty acid esters of glycerol (mono-, Di- and triglycerides), waxes, cholesterol and stearic acid. [Nagpal et al. WJPPS, Vol 5, Issue 03, 2016]. Liposomes are also known excipients, such as traditional liposomes, niosomes, ethosomes and transfersomes Examples of carrier vehicle or matrix materials include:
Paraffin wax with melting point 53° C.-57° C.
Paraffin wax with mp. 58° C.-62° C.
Paraffin wax with mp.>62° C.
Cetyl alcohol having mp. 49° C.
Oxidized PE homopolymer. Low density Oxidized Polyethylene (LDOxPE) homopolymer, marketed as A-C® 629A, in prill form for use in solvent borne coatings as a rheological aid. It also finds use as a metal release agent in PVC. It can also be atmospherically emulsified for use in aqueous applications, such as textiles, lubricants, coatings and inks, to lower the COF and provide surface properties such as mar & abrasion resistance and increased slip.

Polycaprolactone (hereinafter "PCL")—Semi-crystalline, $M_w$=10,000 g/mol, $T_g$=−60° C., Tm=60° C.

Poly(lactic-co-glycolic acid) (hereinafter "PLGA")—Amorphous, Mw=7,000-17,000 g/mol, Tg=42° C.-46° C., Lactide:glycolide ratio at 1:1.

AClyn® 201 Calcium ionomer of an EAA copolymer. A calcium ionomer of an EAA copolymer. Used in some applications as a pigment dispersing agent for masterbatch in polar resin systems due to enhanced compatability with the resin carrier.

VISCOWAX® 122 PE-Wax is a high quality non-oxidised, non-polar polyethylene wax, produced according to a high pressure polymerisation process, CAS: 9002-88-4;

Licowax® PE 520 powder PE wax is a medium-molecular weight, non-polar polyethylene wax;

Luwax® A (BASF); and

DuPont™ Elvaloy® AC 1820 (ethylene methyl acrylate copolymer or "EMAC") used for film coextrusion, compounding and injection molding. Due to its high melt flow rate, it also can be used in extrusion coating/lamination. EMAC has good adhesion to various substrates (OPA, OPP, paperboard, etc.), gives excellent sealing properties and has high filler acceptance.

Biocompatible—this term may refer to such factors as whether the carrier vehicle is biodegradable, biostable, bioinert, non-antigenic, non-immunogenic, specifically immunogenic (possibly useful to address development of immune tolerance, for example by limited exposure to food, pollen and other environmental allergens, antigens or autoimmunogens).

Payload substance—unless specified, this will be referred to as an active pharmaceutical ingredient ("API") however it must be understood that the payload substance may be of a non-pharmaceutical nature, for example, detergent, fertilizer, dye, radioactive substance. The following characteristics are those which one of ordinary skill in the art would look for in an API. While poorly water-soluble APIs are preferable in the use of 'waxy' excipients in order to achieve sustained release, both hydrophilic and hydrophobic substances, drugs and/or biomolecules can be used. For example, where it is desired to produce microspheres of essential oils, which are liquid at room temperatures, one may first use an adsorbent to soak up the essential oils liquid, before adding the adsorbent to the excipient, solid or melt. In this manner, the techniques of vertical drop microsphere disclosed herein can generally be used for API substances which are hydrophilic or which are liquid at room temps. It is important that the API will have thermal stability within the working range expected to be employed for melting the carrier vehicle, but that does not necessarily mean it must have phase state that is identical to the carrier.

A non-limiting and non-exhaustive list of examples of APIs includes:

ibuprofen, ketoprofen, possibly combined with antioxidant such as ascorbic acid, salbutamol sulphate, theophylline, propranolol, acetaminophen, tacrine, pseudoephedrine, heat resistant peptides (such as Gonadotropin-releasing hormone antagonist or insulin), albuterol, heat-stabilized mAbs, glipizide, thiothixene, haloperidol, hydrochlorothiozide, acetylsalicylic acid (ASA), opioids, steroids, and essential oils, chemotherauptic agents, antidotes, heavy metal cherators, vaccine components (live or dead, viral, bacterial, etc.).

Other examples of payload substances can include fertilizers, vitamins, food supplements, dyes, contrast dyes, radiological substances, phase change substrates, biological substances including algae, bacteria, enzymes, catalysts and many others.

Besides carrier vehicle and API, other examples of ingredients which can optionally be added include:

Gelucires (44/14)—a solubility enhancer. Gelucires are polyethylene glycol (PEG) glycerides composed of mono-, di- and triglycerides and mono- and diesters of PEG. They are inert semi-solid waxy amphiphilic excipients with surface-active properties that spontaneously form a fine dispersion or emulsion upon contact with water. Monolithic Gelucire 44/14 structures are prone to prolonged erosion times, thereby slowing down drug dissolution.

Compritol® 888 ATO—Glyceryl behenate is an oil thickener. Improves the homogeneity of powders for easier compression. Results in 100% lipidic, gellified forms with superior heat stability. A natural glyceryl behenate with a number of cosmetic benefits, it is used as a thickening/gelling agent, as a compacting agent for pressed powders (ATO grade), and improves heat stability of emulsions. It allows a chemist to gellify all types of oils Miglyol® 810/812—triglycerides of fractionated plant fatty acids C8 and C10, such as caprylic or capric acid of coconut oil.

Spherical—for purposes of the inventive techniques it is desired that the sphericity of the microspheres is fairly uniform in average over at least 75% of the outer surfaces of the microspheres formed. It is more preferable that the sphericity is uniform in average over at least 85% of the surfaces of the microspheres formed. It is very preferable that uniform sphericity averages at least 95% of the surfaces of the microspheres formed and is most preferable that average uniform sphericity is at least 98% of the surfaces of the microspheres produced. Another measure of sphericity used in this application is that of contact angle, $\theta_c$. The greater than 140° θc is, i.e. the angle of the sphere walls' curvature at the point where it contacts the collecting surface where it comes to rest and upon cooling, the better. θc of 150° and greater are preferred. $\theta_c$ of 165° and greater are more preferred. $\theta_c$ of 170° and greater are most preferred. The spherical characteristic of the microspheres was determined by contact angle measurements after solidification using a CA analyzer machine (OCA 20, from dataphysics). Ten replicates from each batch were measured, and the mean contact angle $\theta_c$ and standard deviation around the mean were determined. The standard deviation of measurement values in our examples was calculated as 100(12.28%/425.57) or about 2.88%. 15% SD of the measurement value or smaller is considered acceptable. It is preferable that the standard deviation value should be less than 10% of the measurement value. SD value of 5% or smaller is highly preferred. Measurement is performed using the tools described in ASTM D7334, taking into account that the standard actually is designated for measuring the surface tension of surfaces using water, whereas the measurements here are for solid spheres on a solid superoleophobic surface.

Super-Oleophobicity—having a low surface energy and roughness. A surface which forms a contact angle $\theta_c$ with the organic liquids of the delivery vehicles of the type used in the techniques disclosed herein which is greater than 150 degrees is preferred. Anything with a lower surface tension than water is less preferable. The superoleophobic surface is preferably maintained at a temperature significantly (up to about 40° lower) cooler than the melting point of the polymer carrier vehicle. The range of "cooler" temperature usually will be from as low as −80° C. up to about 100° C.

General Principles of the Techniques

The disclosed technique overcomes the disadvantages of the prior art by providing a method for producing microspheres, having an average radius of less than 500 μm and having substantially (at least 75%) spherical outer surfaces, consisting of a biocompatible hot-melt carrier vehicle and a payload substance to be delivered, comprising the following procedure;

a. mixing solid carrier vehicle and solid payload substance, b. heating the mixture until at least the carrier vehicle is liquefied and the mixture is turned into a dispersion or solution, c. forming microdroplets by pushing, by application of pulsatile pressure (or by applying constant pressure and cycling between opening and closing an extrusion valve, or some combination of both), the molten carrier vehicle/payload substance solution or dispersion through at least one orifice, into a microdroplet-forming space and onto a collecting surface.

or c. pushing portions of the molten mixture through at least one, but preferably many, orifice (apportionment occurring by pulsatile application of pressure to the molten mixture or by cycling between opening and closing, in the PCL examples below at a nozzle shear rate of 0.35 Hz, an extrusion valve at the orifice while applying constant, but low pressure to the molten mixture), and d. permitting droplets to drip from the at least one orifice into at least one droplet-forming space, possibly comprising a gas atmosphere, and onto a collecting surface which may comprise a solid surface set at a sufficiently great distance (from about 1 mm to about 4 mm) and time (possibly reached via a steeply angled parabolic-like curving surface or trough) from the at least one orifice to permit substantial droplet separation, and sphere formation and solidification to occur.

In another exemplary embodiment gentle non-deforming collection of the still-cooling microdroplets may be achieved by collecting the droplets onto a superoleophobic soft and loose fibrous weave such as an aerogel having a porosity substantially larger and a depth several times the diameter of the desired microspheres through which the microdroplets can gently drop as they finish cooling.

Thermal separation of the superoleophobic surface from the hot-melt droplet ejection apparatus is preferable. This can be done by any number of ways including suspending in the droplet forming space a thermal barrier, such as a film or sheet. That would be selected and constructed to preferably physically and thermally separate all or most of the hot melt apparatus from the relatively "cooler" superoleophobic surface. It is preferable that the tip 70 or tips of the ejection nozzles protrude down through one or more apertures provided in the thermal barrier 200 that do not interfere with the droplet forming process (see FIG. 7D).

In an alternative exemplary embodiment, a method for producing microspheres less than 500 μm in radius that have substantially (at least 75%) spherical outer surfaces comprising a biocompatible hotmelt carrier vehicle and a payload substance to be delivered, where the payload substance has a melting point suitably similar to that of the carrier vehicle, comprises the following procedure;

a. melting carrier vehicle material in one reservoir and, optionally, melting or simply holding payload substance in a thermically separated reservoir;

b. mixing, dissolving or dispersing the payload substance into the molten carrier vehicle in a mixing reservoir; and c. forming microdroplets by pushing, by application of pulsatile pressure (or by applying constant pressure and cycling between opening and closing an extrusion valve, or some combination of both), the molten carrier vehicle/payload substance solution or dispersion through at least one orifice, into a microdroplet-forming space and onto a collecting surface.

Microspheres produced by the techniques described herein having an average size diameter less than about 500 μm, and preferably have an average size diameter less than about 200 μm. More preferably for certain applications and methods and routes of administration, the microspheres should have an average diameter of 801 μm or less. For certain applications, methods and routes of administration, for example for deep inhalation into the lungs, the average diameter of the microspheres produced by the described techniques should be less than 10 μm or even less than about 2 μm in diameter.

Microspheres may be made using the inventive technique where the loading range of payload substance is on average from 50% w/w to about 91% w/w of each microsphere. The examples will illustrate that microspheres of ibuprofen 91% w/w in cetyl alcohol 9% w/w were made having contact angles $\theta_c$ of 170° and having a diameter of 801 μm.

Temp, Viscosity, Pressure

These are all important factors in controlling the volume and speed of the droplet exiting the melt apparatus nozzle. That of course determines the size of the drop, it's "hang time" in the sphere-forming space and its velocity on impact. Even the direction in which the nozzle (or the tube leading to the orifice) is pointing, generally straight down, may have an effect on total velocity or the time for the melt to separate from the nozzle.

Temperature range for melting of polymer carrier vehicle (up to 20° more than glass transition temperature) might be anywhere from about 45° C. to as high as 200° C. It is advantageous for the API to have a similar melting temperature as the carrier vehicle, but in cases where a dispersion is desirable, it is not critical (e.g. dispersion of organic materials in the carrier vehicle or polymer that do not melt at all).

Preferred temps are 80° C.-90° C. to start and can range downwards as low as 45° C. and can go up to about 200° C., depending on the carrier vehicle properties and assuming that the range is tolerable by the API. One important factor is having a melt which ends up near the dispensing nozzle at a temperature which imparts a resultant viscosity that is not so low as to create undesired leakage through the nozzle of the microdispensing valve between dispensing operations. Generally, the viscosities between 100 mPa and 2500 mPa were found to work well and produce acceptable results.

Referring to FIGS. 2A-2E, the equipment used in the Examples is LIQUIDYN's (recently purchased by Nordson EFD) dispensing system, comprised of pressure and temperature controllers, and a micro dispensing valve (see FIG. 2A). The material is placed in a reservoir, melted, transferred by capillaries piping or tunnels and dispensed through changeable types of nozzles. The nozzle's orifice size can currently be varied between 50 μm-150 μm although it is possible that smaller nozzles may be developed. One of the two valves used in the examples is the Liquidyn P-Dot CT®, a pneumatically actuated high performance valve for contactless dispensing of highly viscous materials (50-200,000 mPas). The P-Jet CT® valve is suitable for dispensing low to medium viscosity materials (0.5-10,000 mPas). The viscosities of the melts in the examples ranged from 100 mPa to about 2500 mPas. The viscosity of the melts for the microspheres produced were about 1500 mPa. It should be understood that in scale-up for commercial quantities, it is practical to have an array of such valves operating in synchrony. Additionally, it may be preferred to have an array of ejection valves which can be repositioned rapidly after each ejection operation is timed to have completed, rather than waiting for the microspheres to cool. For example, in FIG. 7A, it is seen that about 46.477 ms elapses when the microdroplet thread actually separates from the nozzle and begins gathering into a microsphere on the cooler superoleophobic surface. Thus, an operator would know to program the ejection valves array to be ready to move to a different ejection position above the superoleophobic surface to begin the next ejection cycle even while the previous microspheres are still forming up and cooling. Looking at FIG. 7D.3, the array can move away from that ejection position while the microsphere in FIGS. 7D.4 et seq. cools to firmness sufficiently to avoid damage from moving the superoleophobic surface.

Superoleophobic surface—aluminum slides were pre-treated by being coated in two stages with a commercially available product, UltraEverDry www.spillcontainment-.com/products/ever-dry/ which in one commercially available product comprises: xylene, naptha, hexane, methylethylketone, and toluene. Another such coating could be cyclopentasiloxane.

Scaleup—Options: [1] using broad area drip-head e.g. 10,000 cm2 and running in millisecond cycles between drips; or [2] using arrays of multiple Liquidyn valves of the type used herein, or using printing heads (multi-jet), possibly even ink-jet printing technology.

In order to achieve uniformity of the excipient and API, premixing of both ingredients was performed in a Brabender® mixer or twin screw extruder, per standard practice.

Vertical drop—experimentally found that 1 mm-2 mm worked with the materials being used and with dropping through ambient air onto a superolephobic surface at room temperature. Use of alternative collection surfaces, such as a superoleophobic funnel or parabolic chute or an aerogel, or changing the atmosphere of the sphere-forming space, by filling with chilled inert gases, are also contemplated.

Dropping each microdroplet into a miniature upwardly directed cold-air similar in concept to a gentle and abrasion-free fluidized bed could increase the rate of microsphere shape stabilization.

It was found that bringing the superoleophobic collection surface temperature up to about Tm (or Tg)–(minus) 20° C., or even to −80° C., the spheres are "more perfect" to begin with, but are somewhat more prone to collapse if left to cool without added external cooling such as forced air for better results.

Column pressure—the pressure applied to the back of the column of hot melt/dispersion. Experimentally, the column pressure was usually on the order of 0.2-0.8 bar.

Valve pressure—this is the pressure applied to the nozzle valve which controls the rate at which the nozzle opens and closes—and hence it controls the amount of time the valve will be open to let melt flow. This pressure was generally kept at 2.0 bar for the examples, but it will vary with the viscosity of the particular melt/dispersion of the carrier vehicle/API combination.

The combination of melt viscosity, column pressure, valve pressure and nozzle size (the examples used nozzles of 701 μm and 150 μm) will determine the size of the microdroplets and hence the size of the resulting microspheres.

The invention provides for allowing microsphere stabilization on the superoleophobic surface. Time of sphere shape stabilization is from a mere tens of microseconds to less than 120 seconds, preferably less than 60 seconds and most preferably less than 10 seconds.

Ways of forming droplets—In exemplary embodiment, a single nozzle is illustrated in a vertical orientation and vertically dropping microdroplets to form microspheres as they fall. While in other exemplary embodiments, melt or dispersion can be squeezed through pores, mesh, screen, sintered metal filter whereby a plurality of droplets are formed and dropped (ejected or separated) as nearly simultaneously as possible, it is believed that the disclosed arrangement provides a highly desirable degree of quality control. Therefore, an array of ejection valves, or a showerhead type system is viewed as the most logical scale-up device.

Microdroplets may be ejected from the nozzle into a controlled atmosphere: vacuum, nitrogen, argon, xenon, low humidity, low temperature, super-cooled.

Sphere size may be influenced and hence controlled by [a] careful control and variation of the melt temperature; i.e. increasing melt temperature generally reduces viscosity thereby increasing flow rate and requiring greater control of the opening and closing speed of the nozzle valve opening and closing; [b] increasing or decreasing pressure column pressure or valve pressure; or [c] controlling impact speed of sphere on surface (for example dropping spheres a distance of about 2 mm and having them gradually contact the upper portion of a superoleophobic curving slope, like a curved funnel—ski-jumping for microspheres).

Sizing

The desired size of the resulting microspheres is dependent on the anticipated use to which they will be put, and, in the case of drug delivery, the desired mode of administration. For example, are they to be inhaled—orally or nasally. Microspheres which must penetrate into bronchioles will need to be less than 10 μm in diameter, preferably less than 5 μm, and most preferably less than 2 μm.

In another exemplary embodiment (not shown), in place of dropping onto a solid superoleophobic surface, the microdroplets can be dropped through the sphere-forming space onto a thickness of one ply or multi-ply large-weave superoleophobic aerogel through which the microspheres can bounce safely through while they cool without being deformed by striking a solid surface.

Figure 3A:
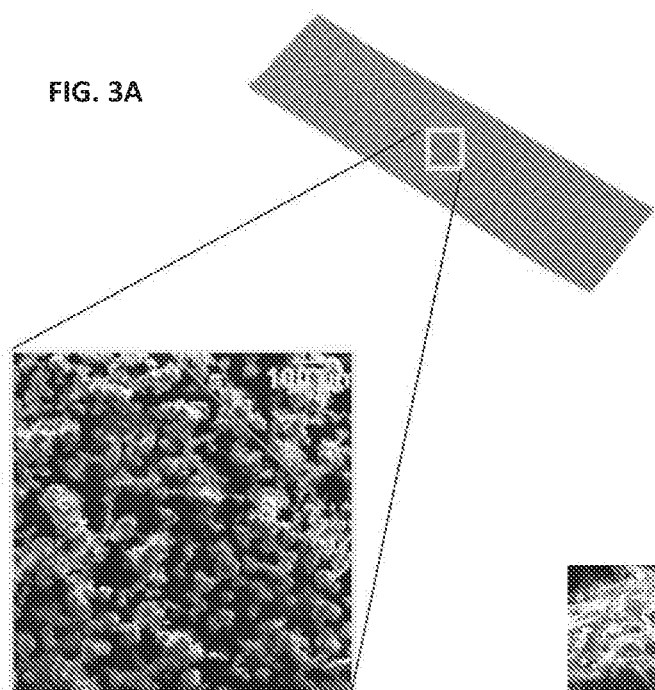
FIG. 3A shows a scanning electron micrograph of a superoleophobic surface of the type used to practice embodiments of the invention.
Figure 3B:
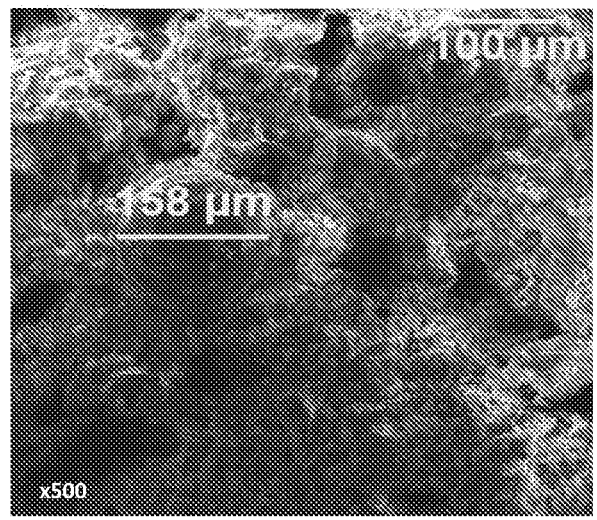
FIG. 3B shows a microsphere prepared from oxidized PE wax particles, marketed as A-C 629, melted at 130° C., using an ejection nozzle size 701 µm, P1: 0.3-0.8 bar P2: 2.0 bar, Tappet setting: 6 clicks.
Figure 3C:
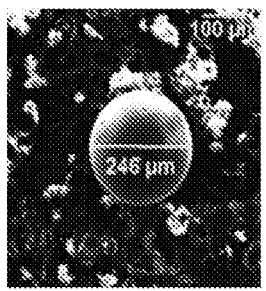
FIG. 3C shows a cetyl alcohol microsphere, produced from 1 gr of CA deposited inside the reservoir, melted at 80° C., tappet set to 4 clicks.

Reference is now made to FIG. 3C, which is a photo of a 246 μm microsphere produced in accordance with an embodiment of the disclosed technique. The materials and conditions for producing this example were as follows: polyethylene wax particles, A-C® 629, melted at 130° C.; dispensed through nozzle size 70 micron, also heated to temp. 130° C., column pressure P1: 0.3-0.8 bar, nozzle valve pressure P2: 2.0 bar, Tappet spring setting: 6 clicks.

Figure 3D:
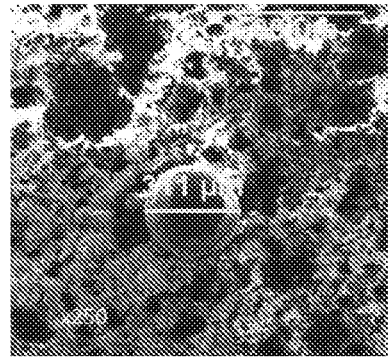
FIG. 3D shows a microsphere formed from ibuprofen 91% by weight in cetyl alcohol 95 by weight using the techniques of the disclosed invention having a diameter of 158 µm.

Reference is now made to FIG. 3D, which is a photo of a 311 μmm cetyl alcohol microsphere produced in accordance with an embodiment of the disclosed technique. The materials and conditions for producing this example were as follows: 1 gr of CA deposited inside the reservoir, melted at 80 deg., set tappet to 4 clicks;

Reference is now made to FIG. 3B, which is a photo of a 158 μmm microsphere of ibuprofen in cetyl alcohol produced in accordance with an embodiment of the disclosed technique. The materials and conditions for producing this example were as follows: ibuprofen 91% w/w in cetyl alcohol (CA) 9% w/w using the techniques of the disclosed invention.

Figure 4B:
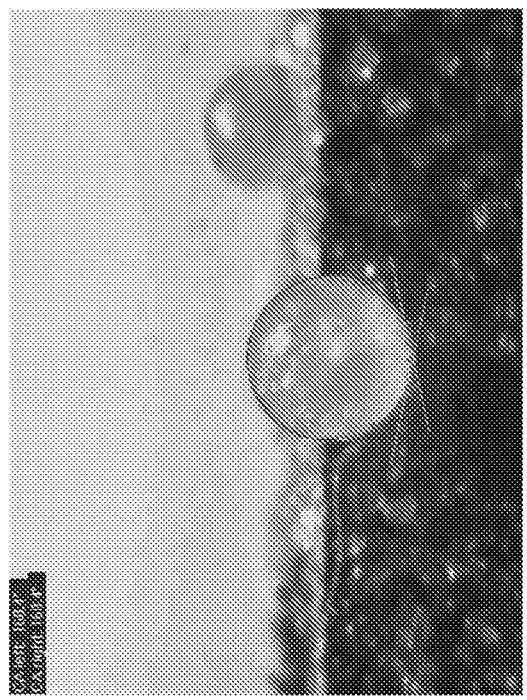
FIG. 4B shows a polycaprolactone microsphere produced by the techniques of the invention; and having contact angle $\theta_c$ of 168.4° made using a needle nozzle sized 150 µm at melting temperature of 150° C., P1: 0.2 bar, P1: 2.5 bar, tappet: 4 knurls and superoleophobic surface having ambient temperature of room temperature, about 25° C., about 1200 mPas nozzle viscosity.
Figure 4A:
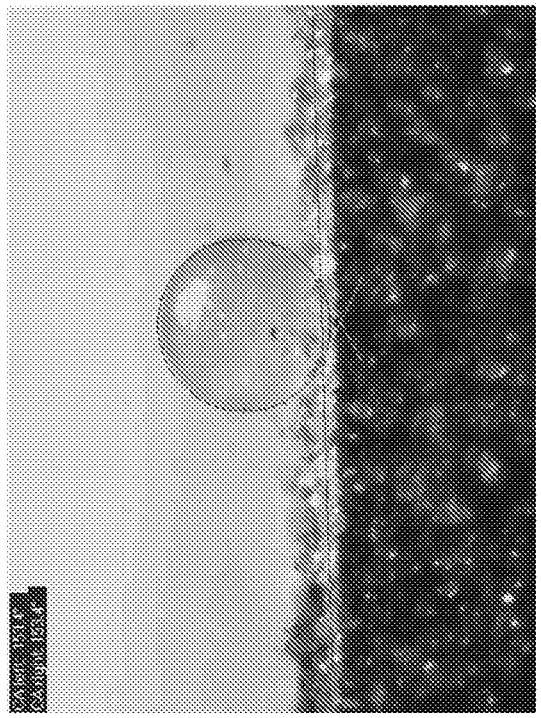
FIG. 4A shows a polycaprolactone microsphere produced by the techniques of the invention and having $\theta_C$ of 153.4° made using a needle nozzle sized 150 µm at melting temperature of 150° C., P1: 0.2 bar, P1: 2.5 bar, tappet: 4 knurls and superoleophobic surface having ambient temperature of room temperature, about 25° C., about 1200 mPas nozzle viscosity.
Figures 8A, 8B, 8C:
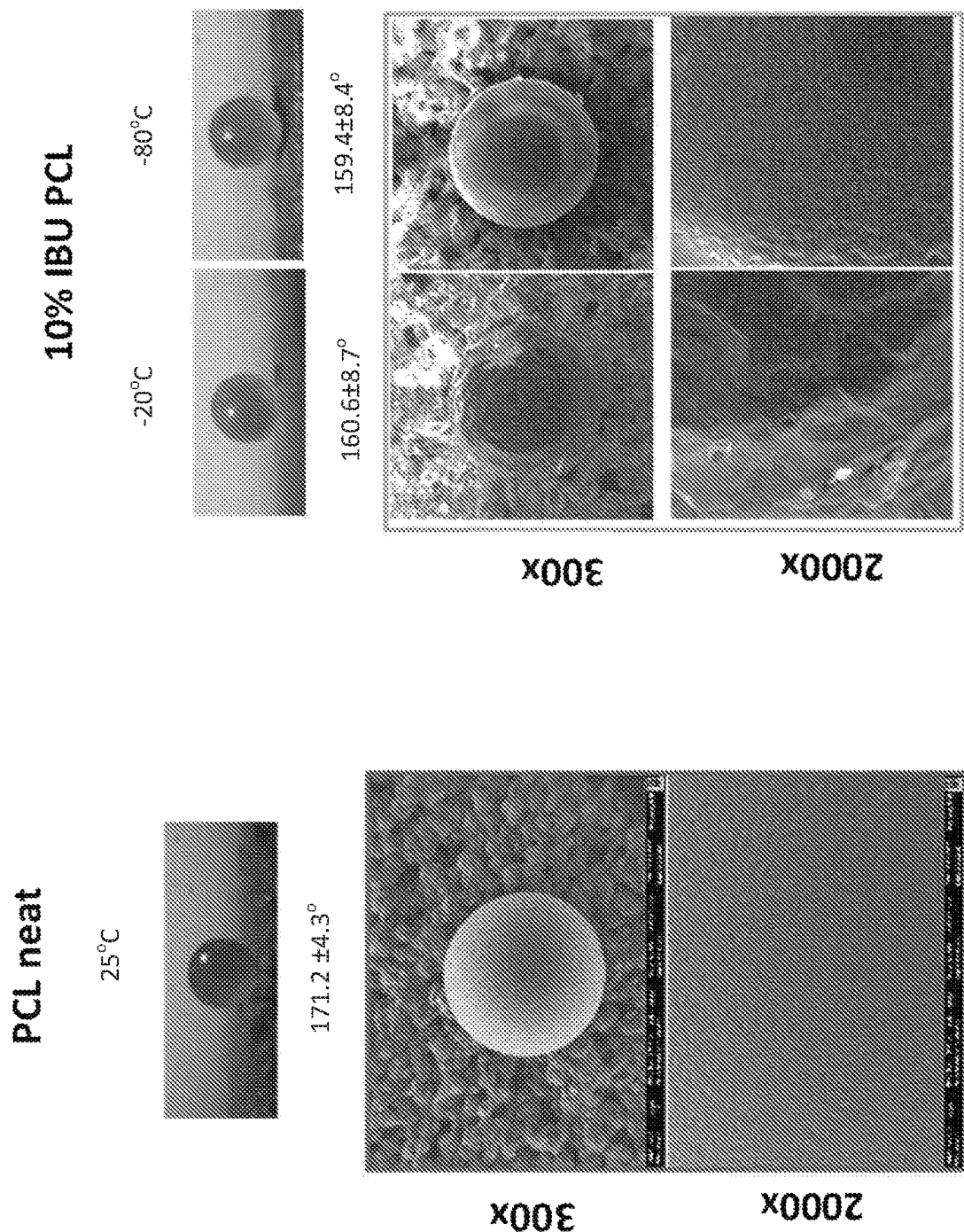
Figure 9A:
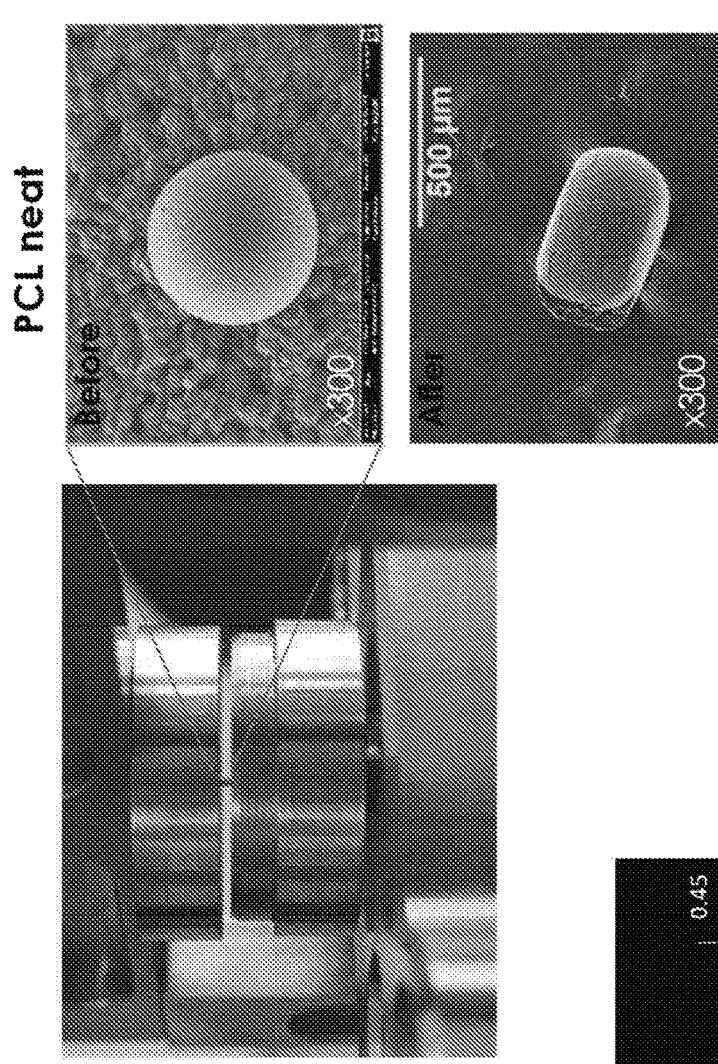
FIGS. 9A-9C show compression data on PCL microspheres and IBU-PCL microspheres made using the disclosed techniques.
Figure 9B:
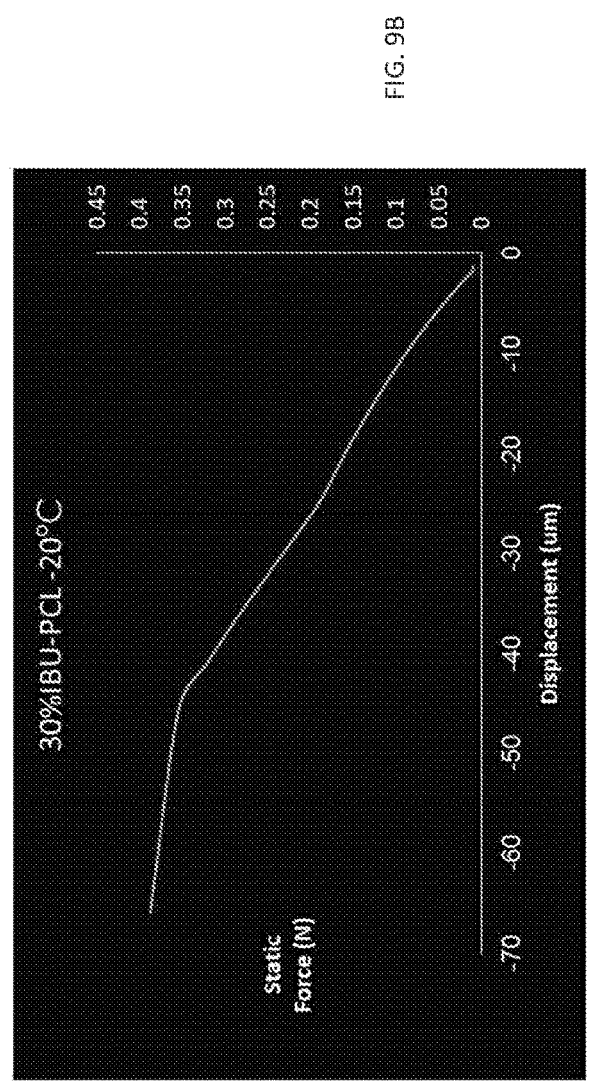
Figure 9C:
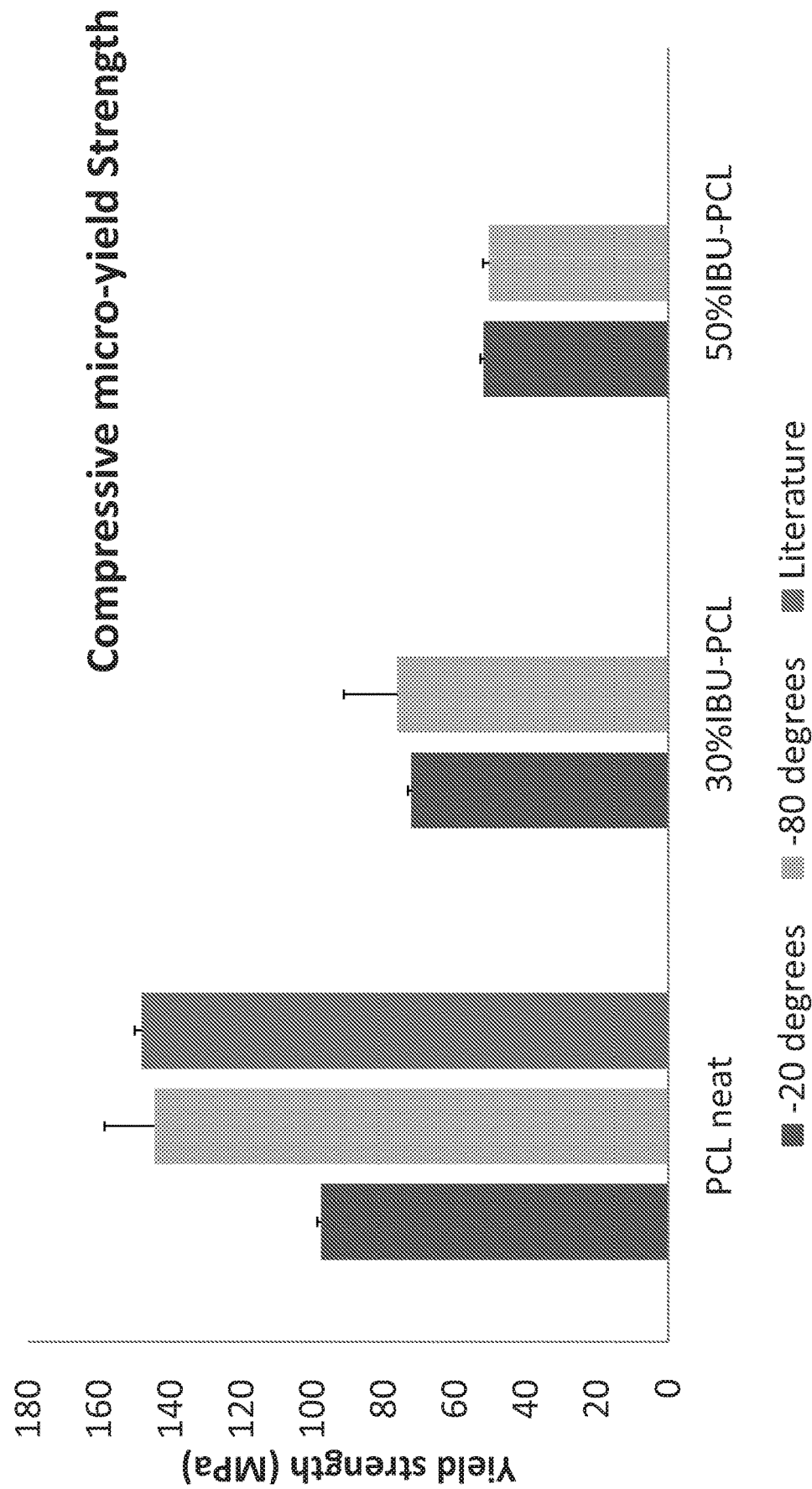

Reference is now made to FIG. 4A, which is a photo of a PCL microsphere produced in accordance with an embodiment of the disclosed technique. The materials and conditions for producing this example were as follows: polycaprolactone microsphere produced by the techniques of the invention and having contact angles $\theta_c$ of 153.4° made using a needle nozzle sized 150 μm at melting temperature of 150° C., Column pressure P1: 0.2 bar, P1: 2.5 bar, tappet: 4 knurls and superoleophobic surface having ambient temperature of room temperature, about 25° C.

Reference is now made to FIG. 4B, which is a photo of a microsphere produced in accordance with an embodiment of the disclosed technique. The materials and conditions for producing this example were as follows: a polycaprolactone microsphere produced by the techniques of the invention; and having contact angles of 168.4° made using a needle nozzle sized 150 micron at melting temperature of 150° C., P1: 0.2 bar, P1: 2.5 bar, tappet: 4 knurls and superoleophobic surface having ambient temperature of room temperature, about 25° C.

Reference is now had to FIGS. 5A-5C which show the parameters and dissolution rate data generated using microspheres produced using the techniques of the present invention and having Rhodamin dye incorporated therein in place of an API.

Reference is now had to FIGS. 7D.1-7D.6 which is a sequence of frames taken from high speed video. The elapsed time from the beginning of the microdroplet separation from the dispensing nozzle in FIG. 7D.1, to the time the microsphere fully cools in FIG. 7D.6 is about 6 seconds to about 8 seconds. The contact angle of the resultant microsphere is about 168°. Higher contact angles are seen in the microspheres shown in FIGS. 8A-8G.

The efficiency (material loss) of the above-described techniques is very high compared to aerosolization or fluidized bed spheronization, techniques which struggle to achieve efficiencies of 50%. By comparison, the disclosed techniques have efficiencies easily exceeding 60%, usually achieving 95% or more (i.e. little of the payload material is lost in the process).

Example with Essential Oils and other room-temperature liquids

For delivery of essential oils, and most other substances which generally are and remain liquid at room temperature, the essential oils can be absorbed by the polymer in the melt state, and when cooled, the polymer solidifies and the oils slowly diffuse out of it. To improve the loading capabilities of such a system, one can use inorganic absorbents (i.e. fumed silica) to absorb the oil as a preliminary step prior to adding the inorganic adsorbent to the polymer melt. Such a combination has the combined effect of increasing the amount of absorbed oils as well as further increasing the release profile possibilities.

Referring again to FIGS. 6 and 7, the present solvent-free method teaches printing of microspheres directly from melt, eliminating most of the shortcomings of today's techniques. An ink-jet-like system, shown in FIGS. 2A-2E, generates individual melt droplets which drop vertically from each nozzle. The droplet interact with a super-oleophobic non-wetting surface seen in FIG. 2F, gather into a substantially spherical shape under surface tension and solidify. Documented by a high-speed camera, it is evident that a filament-breakup phenomena occurs prior to the sphere forming, a first observation in polymer melts. Firstly, the column pressure and heating allows capillary forces in the nozzle or orifice to be overcome by the melt, and a filament is formed. Secondly, the filament thins and pinches-off at a singular point under highly viscous and elastic regime, exhibiting large Ohnesorge (Oh), Elasto-capilary (Ec) and Intrinsic Deborah (Deo) numbers. Lastly, the low surface tension of the melt surface allows the initial formation of a spherical shape of the filament (high apparent static contact angle), then a droplet is formed and ends up in a quasi-equilibrium shape as a result of short distance impact and spreading time at high temperatures compared with the solidification time.

Referring to FIGS. 8A-8G, it is shown that under different cooling temperatures (25, −20 and −80° C.), PCL loaded with 10-50% ibuprofen (IBU) produced spherical microspheres (154°-176°) with size ranging from 350±7-480±15 μm, with 87% to 100% loading efficiencies, and a method yield of 100%. DSC measurements revealed that with the introduction of IBU, the PCL melting point was decreased (from 53° C. to 47° C.). At low IBU contents, there was no evidence for IBU crystallization. However, PCL's degree of crystallinity was decidedly greater with IBU compared to the neat PCL, and decreased with the increasing amount of IBU in the blend.

Figure 10A:
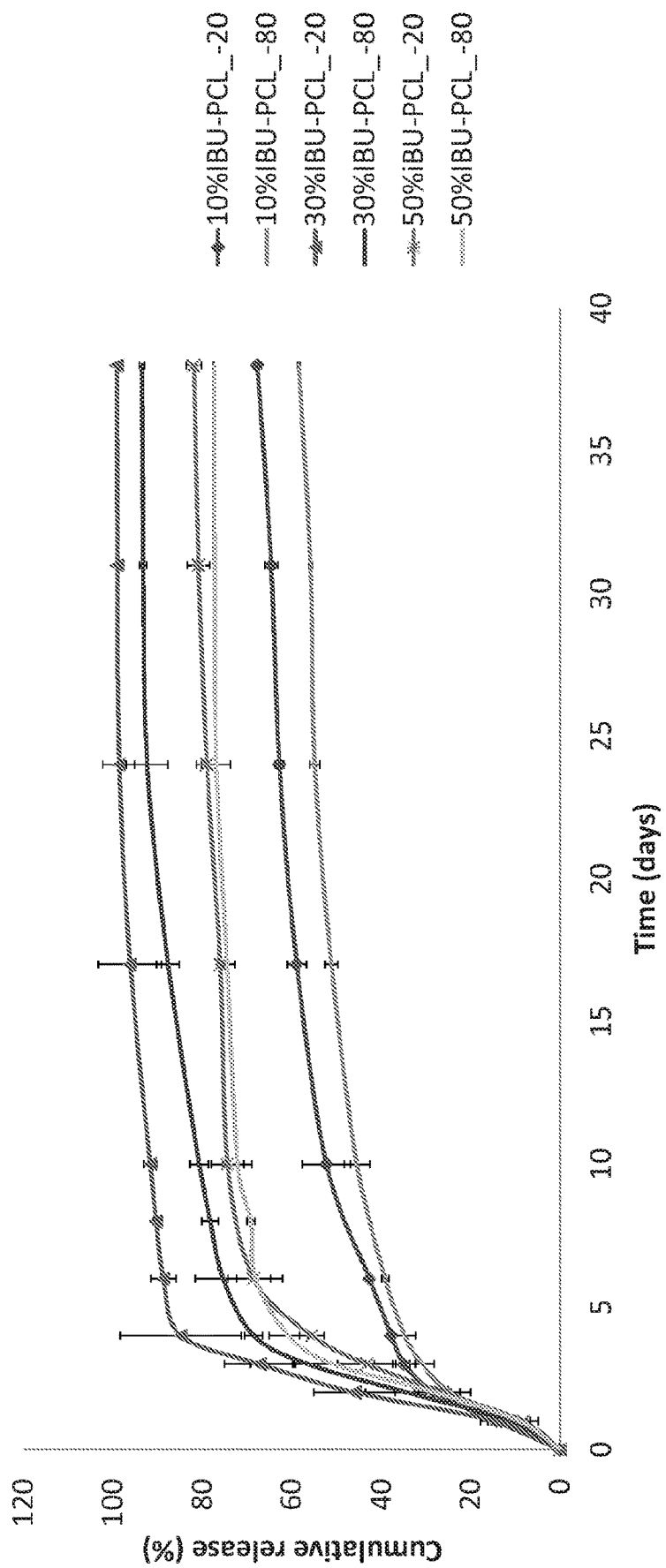
FIGS. 10A-10D show drug loading and release profile data of of IBU-PCL microspheres and IBU-PLGA microspheres made according to the disclosed techniques.
Figure 10B:
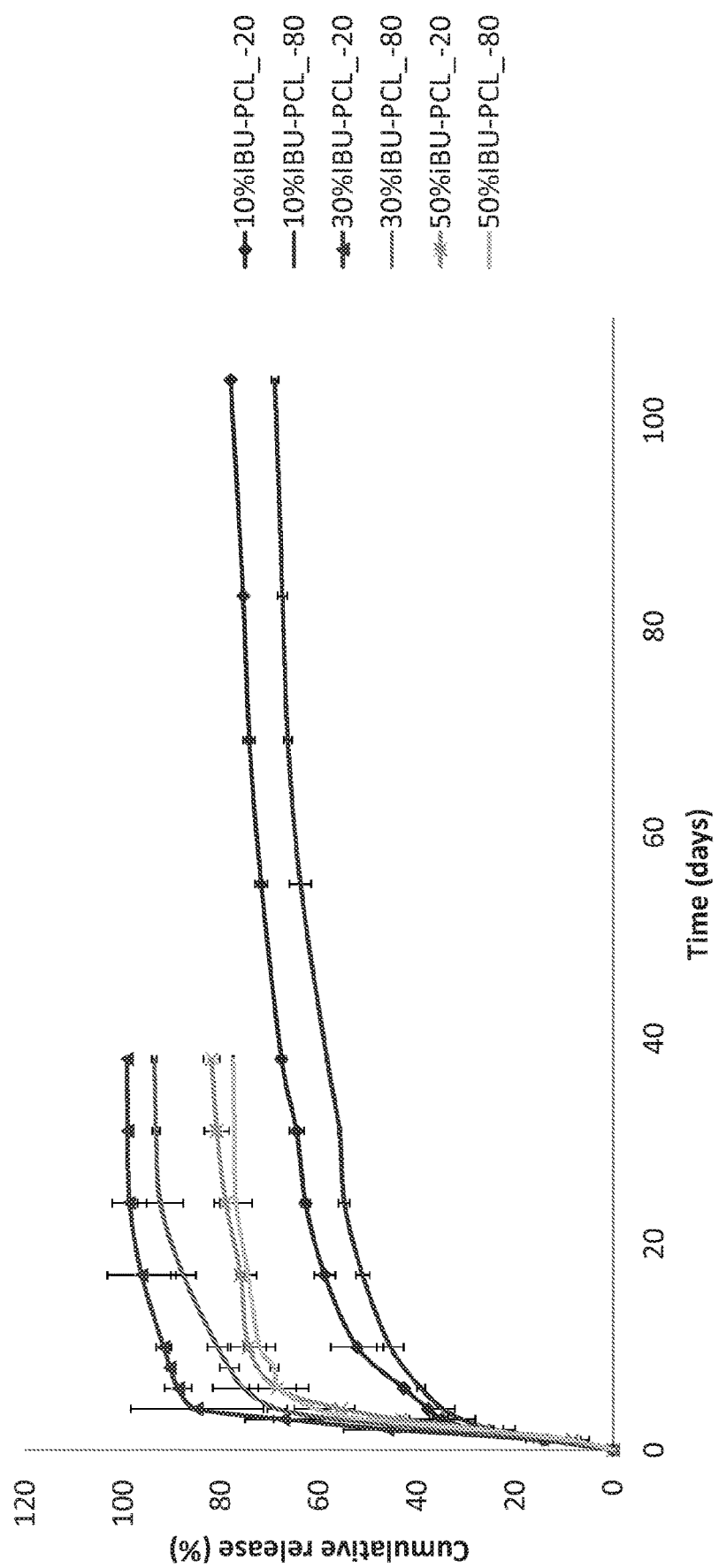
Figure 10C:
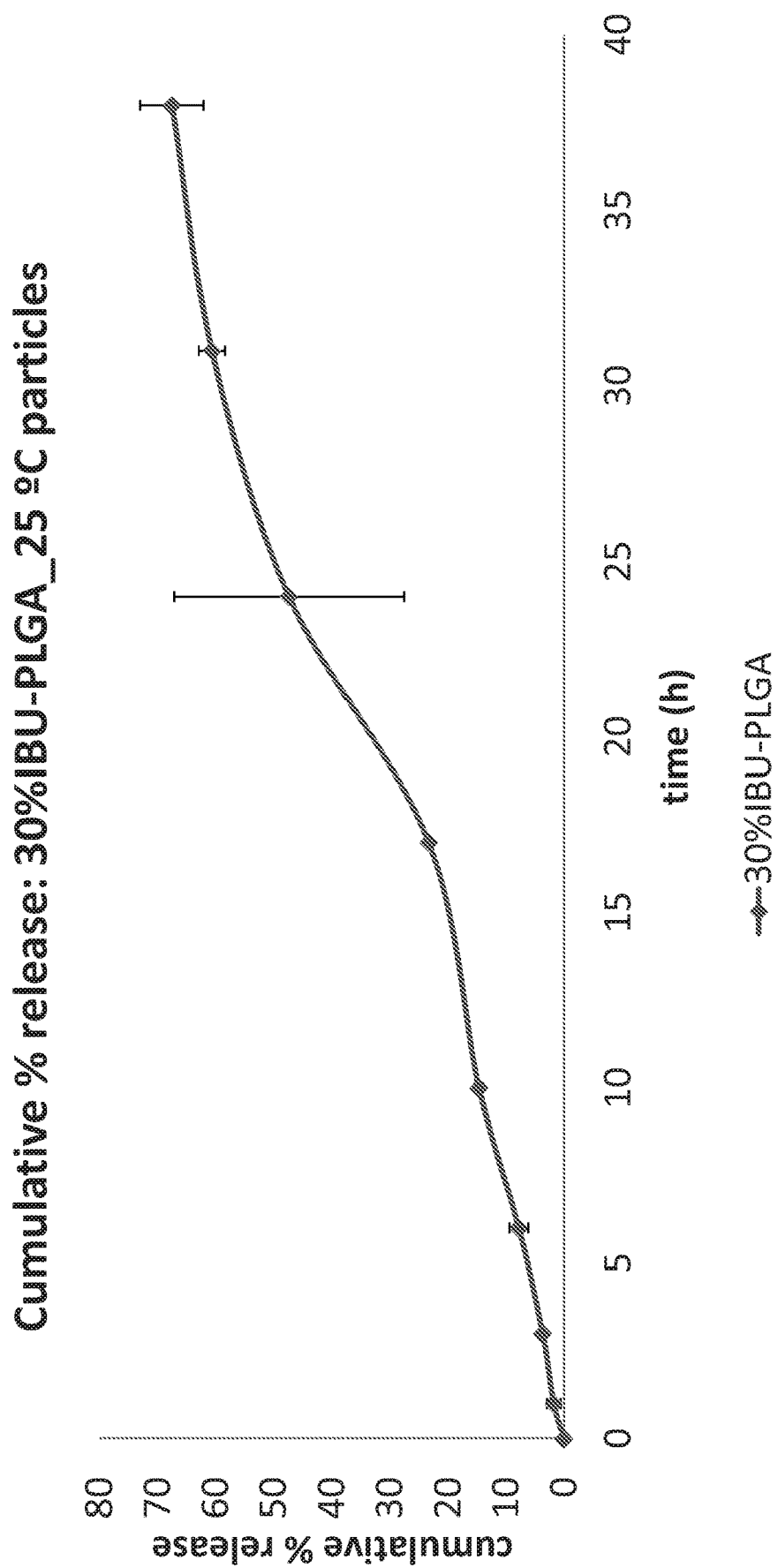
Figure 10D:
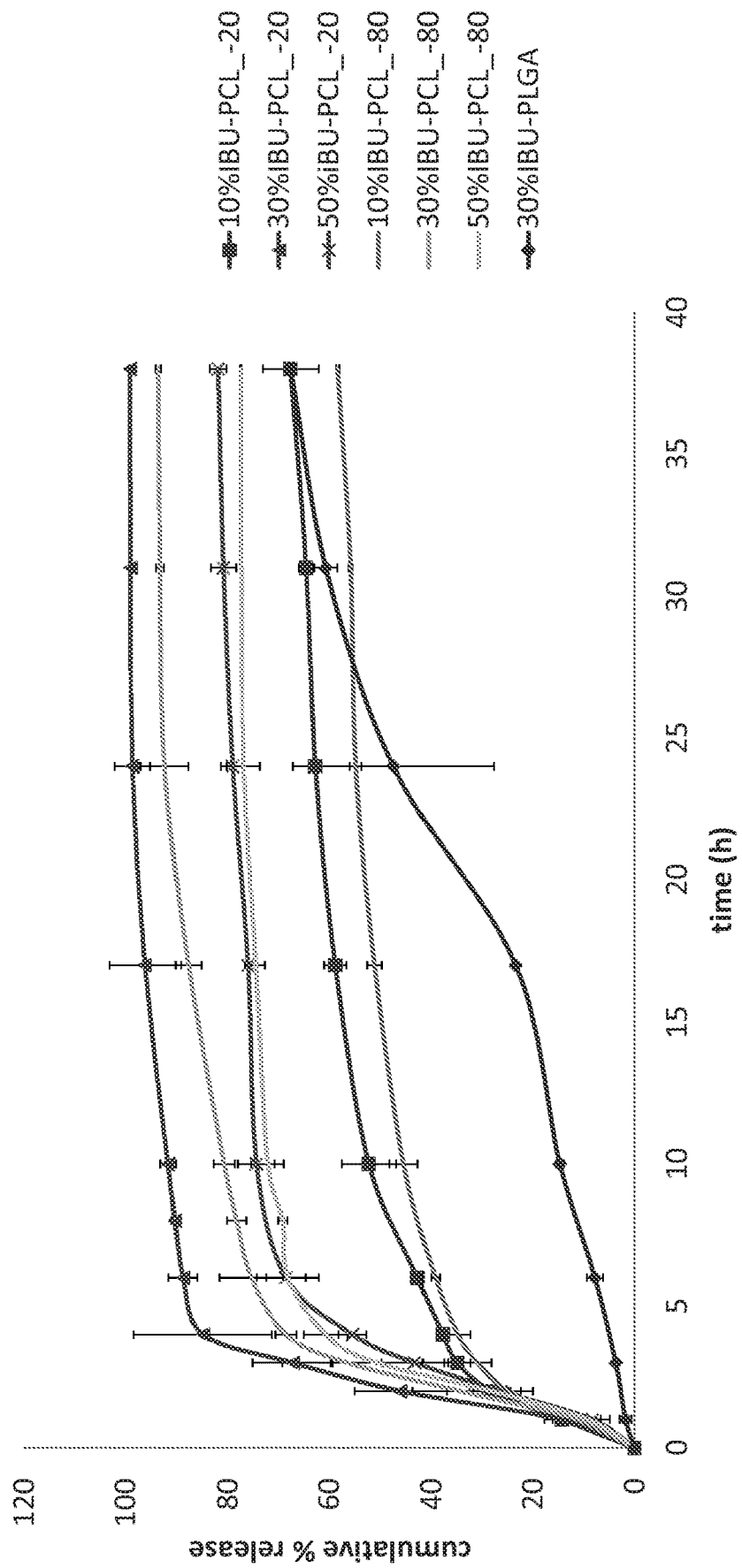

Referring to FIGS. 10A-10D the release profiles as a function of cooling temperature followed an Early time approximation behavior whilst the plateau part corresponds to the Late time approximation. Without wishing to be bound by any particular theory, the competition between the crystallization of IBU and PCL may control the conspicuous difference in the obtained release profiles for the varying microspheres, and can be correlated with thermodynamic evaluations. As mentioned hereinabove, most importantly FIGS. 10C and 10D show that first degree or zero-order release profile is made using 30% IBU-PLGA and took 38 days to release about 60% of the API.

This application describes a method for producing polymeric microspheres directly from melt by carefully dropping them onto superoleophobic surfaces. The resulting API-loaded polymer microspheres exhibit (1) reproducible size and spherical shape, (2) controlled release kinetics fitting literature models, and (3) high drug encapsulation efficiencies with a high process yield (~100%).

Reproducibility

Table 1 shows the results for reproducibility in size for the microspheres. About microspheres from two different batches were produced from 30% IBU-PCL and cooled at −20° C. Average diameter was calculated and the standard deviation around the mean as well.

TABLE 1

|    | A[μm]  | B      |
|----|--------|--------|
| 1  | 398.34 | 435.68 |
| 2  | 423.24 | 436.70 |
| 3  | 425.33 | 439.91 |
| 4  | 431.54 | 435.69 |
| 5  | 427.41 | 448.14 |
| 6  | 443.99 | 419.17 |
| 7  | 425.31 | 439.85 |
| 8  | 419.09 | 438.72 |
| 9  | 435.70 | 419.11 |
| 10 | 421.58 | 414.65 |
| 11 | 435.78 | 448.13 |
| 12 | 406.64 | 466.77 |

TABLE 1-continued

|      | A[μm]  | B      |
|------|--------|--------|
| 13   | 431.54 | 452.86 |
| 14   | 385.90 | 466.97 |
| 15   | 404.57 | 431.71 |
| 16   | 433.65 | 446.06 |
| 17   | 437.80 | 462.04 |
| 18   | 446.08 | 448.31 |
| 19   | 425.32 | 450.79 |
| 20   | 398.34 | 439.71 |
| 21   | 413.12 | 458.98 |
| 22   | 425.32 |        |
| avg. | 425.57 | 441.65 |
| S.D. | 12.28  | 13.53  |

It will be appreciated by persons skilled in the art that the disclosed technique is not limited to what has been particularly shown and described hereinabove. Rather the scope of the disclosed technique would be defined only by claims, similar to, but not limited in scope by the examples which follow.

What is claimed is:

1. A method for producing a plurality of microsphere having an average diameter of less than 500 μm in diameter and an average contact angle θc greater than 140°, the method comprising:
heating and mixing a polymeric carrier vehicle with at least one payload substance to obtain a molten mixture free of organic solvent; dispensing microportions of the molten mixture through an orifice of a droplet-forming space onto a solid superoleophobic surface; and
allowing the dispensed microportions to stabilize on the superoleophobic surface,
wherein said polymeric carrier vehicle is biocompatible and has a melting point of about 45° C. to 200° C.;
wherein the payload has a melting point suitable to be dissolved or dispersed in the molten mixture;
wherein the payload has thermal stability in the molten mixture;
wherein the payload is solid or liquid at room temperature;
wherein said molten mixture has a viscosity between about 100 mPas and about 2,500 mPas;
wherein stabilization of the microportions is within a time period of a fraction of a second, whereby said plurality of microspheres are formed.

2. The method of claim 1, wherein said polymeric carrier vehicle is heated to form a hot-melt carrier and subsequently mixed with the at least one payload substance into a molten dispersion or solution.

3. The method of claim 1, wherein said polymeric carrier vehicle is mixed with the at least one payload substance and subsequently heated into a molten dispersion or solution.

4. The method of claim 1, wherein said polymeric carrier comprises poly(lactic-co-glycolic acid) (PLGA) and said payload comprises essential oil.

5. The method of claim 1, comprising dispensing said molten mixture through said droplet-forming space having a nozzle orifice size of between 50 μm-150 μm.

6. The method of claim 1, wherein the superoleophobic surface is at room temperature.

7. The method of claim 1, wherein the superoleophobic surface is maintained at a temperature below 0° C.

8. The method of claim 1, wherein said microdroplets are formed by any one of (i) pushing, (ii) applying pulsatile pressure, and (iii) applying constant pressure and cycling between opening and closing an extrusion valve on the molten mixture when the molten mixture is dispensed through said orifice.

9. The method of claim 1, wherein the drop-forming space is a vacuum or filled with one or more gases selected from the group consisting of air, nitrogen, argon, and xenon.

10. The method of claim 1, wherein each microsphere within the plurality of microspheres comprise a mixture of polymeric carrier vehicle and a payload substance;
  at least 75% of the plurality of microspheres having a uniform spherical surface;
  at least 75% of the plurality of microspheres have a contact angle θc greater than 140°.

11. The method of claim 1 wherein a thermal barrier is suspended in the droplet forming space above the superoleophobic surface, at a height at least 100 μm greater than the average diameter of the microspheres.

12. The method of claim 1, wherein the polymeric carrier vehicle comprise a member selected from the group consisting of polylactic acid, Poly(lactic-co-glycolic acid) (PLGA), polycaprolactone (PCL), cetyl alcohol, oxidized polyethylene (PE), and waxes.

13. The method of claim 1, wherein the payload substance comprises oil.

14. The method of claim 1, wherein said microportions of molten mixture are dispensed through said droplet-forming space with a distance between an ejection nozzle and the superoleophobic surface sufficiently short to allow the molten mixture to reach the superoleophobic surface in a molten state.

15. The method of claim 14, wherein the distance between the ejection nozzle and the superoleophobic surface is less than 4 mm.

16. The method of claim 14, wherein the drop-forming space between the ejection nozzle and the superoleophobic surface is less than 2 mm.

* * * * *